(12) United States Patent
Schöllhorn et al.

(10) Patent No.: US 6,413,208 B1
(45) Date of Patent: Jul. 2, 2002

(54) MEDICAL INSTRUMENT AND METHOD FOR ENDOSCOPIC REMOVAL OF THE SAPHENOUS VEIN

(75) Inventors: Joachim Schöllhorn; Friedhelm Beyersdorf; Christoph Lutz, all of Freiburg (DE)

(73) Assignee: Karl Storz GmbH & Co. KG (DE)

( * ) Notice: Subject to any disclaimer, the term of this patent is extended or adjusted under 35 U.S.C. 154(b) by 0 days.

(21) Appl. No.: 09/504,777

(22) Filed: Feb. 11, 2000

Related U.S. Application Data

(63) Continuation of application No. PCT/EP99/04185, filed on Jun. 17, 1999.

(30) Foreign Application Priority Data

Jun. 19, 1998 (DE) ......................................... 198 27 360

(51) Int. Cl.⁷ ................................................. A61B 1/06
(52) U.S. Cl. ....................... 600/164; 600/131; 600/183; 600/235; 606/190
(58) Field of Search ................................ 600/164, 131, 600/183, 114, 105, 235, 129; 606/159, 190

(56) References Cited

U.S. PATENT DOCUMENTS

| | | | | | |
|---|---|---|---|---|---|
| 4,267,828 A | * | 5/1981 | Matsuo | ........................... | 128/6 |
| 4,294,234 A | * | 10/1981 | Matsuo | ........................... | 128/6 |
| 5,899,913 A | * | 5/1999 | Fogarty et al. | ............. | 606/159 |
| 5,902,315 A | * | 5/1999 | DuBois | ...................... | 606/190 |
| 5,913,818 A | * | 6/1999 | Co et al. | ..................... | 600/204 |
| 5,922,004 A | * | 7/1999 | DuBois | ...................... | 606/190 |
| 5,972,010 A | * | 10/1999 | Taheri | ........................ | 606/159 |
| 6,033,361 A | * | 3/2000 | Co et al. | ..................... | 600/210 |
| 6,036,713 A | * | 3/2000 | Kieturakis | ................... | 606/190 |
| 6,042,538 A | * | 3/2000 | Puskas | ........................ | 600/114 |
| 6,129,661 A | * | 10/2000 | Iafrati et al. | ................ | 600/121 |
| 6,139,489 A | * | 10/2000 | Wampler et al. | ............ | 600/109 |
| 6,193,653 B1 | * | 2/2001 | Evans et al. | ................ | 600/210 |
| 6,196,968 B1 | * | 3/2001 | Rydin et al. | ................ | 600/210 |
| 6,206,823 B1 | * | 3/2001 | Kolata et al. | ............... | 600/129 |
| 6,228,024 B1 | * | 5/2001 | Co et al. | ..................... | 600/204 |
| 6,228,025 B1 | * | 5/2001 | Hipps et al. | ................ | 600/213 |

* cited by examiner

Primary Examiner—Linda C. M. Dvorak
Assistant Examiner—Jocelyn Ram
(74) Attorney, Agent, or Firm—St. Onge Steward Johnston & Reens LLC

(57) ABSTRACT

A medical instrument for endoscopic removal of the saphenous vein has an elongated shaft which has at the distal end a spatula tip and in whose proximal region is arranged a laterally projecting handle. The instrument further has an endoscopic optical system which has an eyepiece cup that is arranged at the proximal end of the instrument. The handle is joined to the shaft in such a way that an outer side of the instrument facing away from the handle continuously has a surface that, from the distal to the proximal end, is free of projections. The eyepiece cup is arranged in oblique orientation with respect to a longitudinal center axis of the shaft and encloses with the handle, with respect to the longitudinal center axis, an angle of less than 90°.

13 Claims, 3 Drawing Sheets

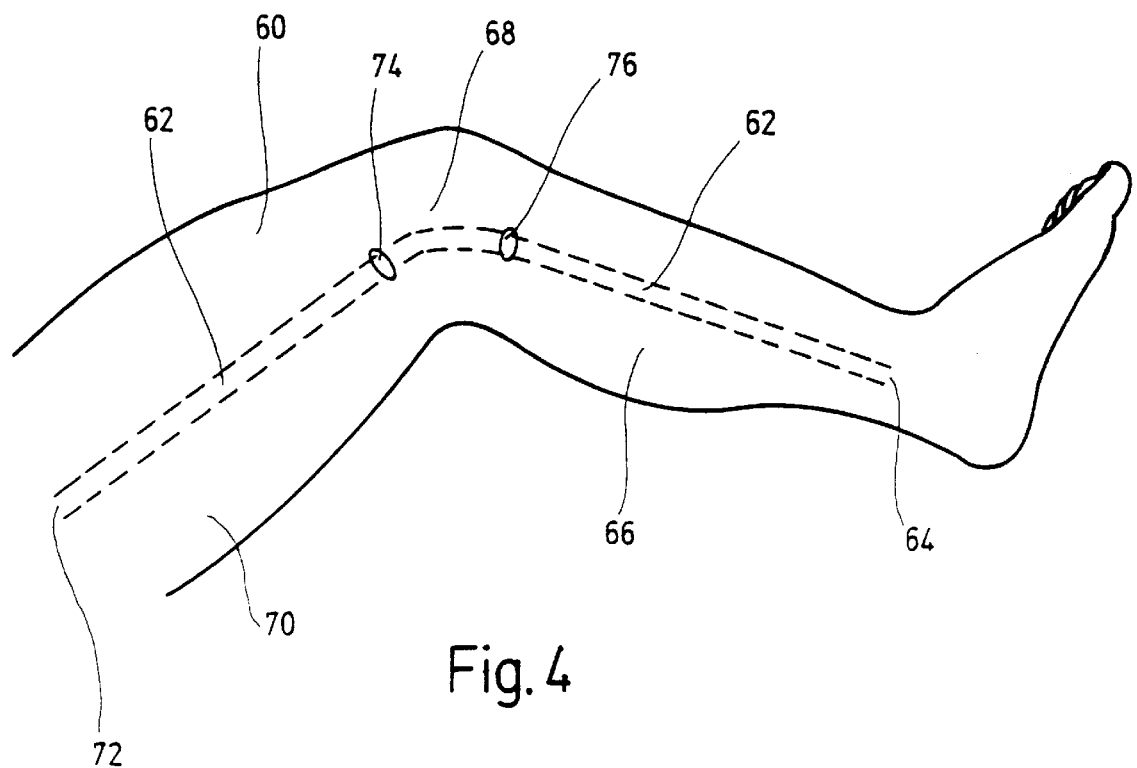
Fig. 4
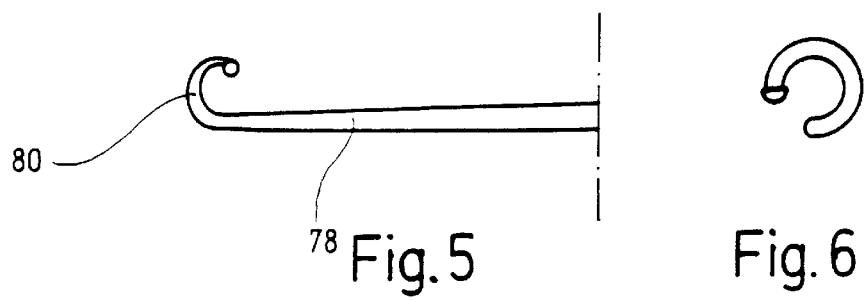 
Fig. 5　　　　Fig. 6

MEDICAL INSTRUMENT AND METHOD FOR ENDOSCOPIC REMOVAL OF THE SAPHENOUS VEIN

CROSS REFERENCE TO PENDING APPLICATION

This application is a continuation of pending International application PCT/EP99/04185 filed Jun. 17, 1999.

BACKGROUND OF THE INVENTION

The present invention relates to a medical instrument for endoscopic removal of the saphenous vein, having an elongated shaft which has at the distal end a spatula tip and in whose proximal region is arranged a laterally projecting handle; and further having an endoscopic optical system which has an eyepiece cup that is arranged at the proximal end of the instrument.

The present invention further relates to a method for endoscopic removal of the saphenous vein.

An instrument of the aforesaid kind is known from the company document "Endo World," CHIR No. 4-D, 1997, published by Karl Storz GmbH & Co., Tuttlingen, Germany. An instrument of this kind is illustrated on page 3 of this document under the designation "optical retractor."

The saphenous vein (vena saphena magna) is a long leg vein that runs on the medial (i.e. inner) side of the leg from the inside of the ankle along the lower leg and thigh to the groin.

The saphenous vein is often removed for use as a transplant in cardiac and vascular surgery. In conventional surgical methods for removal of the great saphenous vein, either a single long incision is made along the inner side of the leg, or several short incisions, separated from one another, are made. Using instruments (called "vein dissectors") introduced through these incisions, the saphenous vein is detached from the surrounding connective tissue and its lateral branching vessels. The detached and isolated vein is then removed through the incision or incisions. This hitherto usual manner of removal through a single long incision or several separate incisions entails the risk, however, of injury to the medial lymph bundle and thus infection of the operative area.

The article "Minimally invasive, video-assisted vein harvesting for cardiac and vascular surgical procedures" by Lutz et al. (1997), in European Journal of Cardio-Thoracic Surgery 12, pp. 519–521, describes an alternative method for removing the saphenous vein, in which the vein is removed using minimally invasive techniques under endoscopic observation. For this purpose, only a single small (2–3 cm long) incision is introduced in the vicinity of the knee joint. Through this incision, the instrument cited initially is introduced upward along the thigh portion of the vein into the groin, and downward along the lower-leg portion of the vein to the inner ankle. The vein is thereby detached from connective tissue and lateral branching vessels, and the entire vein is pulled out through the single incision in the knee region. This endoscopic removal technique is gentle on the tissues, as compared to the earlier removal method described above, because only the one incision is required, and the patient's postoperative discomfort and the risk of surgical infection are much lower. In addition, removal using this newer method always takes place under endoscopic visual supervision.

The instrument known from the aforementioned German company document. "Endo World," which is suitable for the procedure described above, has an elongated shaft that carries at its proximal end a laterally projecting handle and an eyepiece cup belonging to an endoscopic optical system. The shaft is configured from the proximal to the distal end—at which a narrow spatula tip, tapering in the distal direction and slightly curved, is configured—as an approximately kidney-shaped trough for external reception of an optical shaft of the endoscopic optical system, i.e. the endoscope shaft rests on the outside of the shaft in the trough. The endoscopic optical system, made up of the optical shaft and eyepiece with eyepiece cup, can be removed from the shaft by pulling the endoscopic optical system in the proximal direction off the shaft, through an attachment segment of the handle. The shaft of the medical instrument is approximately 30 cm long in order to be able to reach the ends of the vein from the single incision in the knee region.

With the known instrument, the handle is attached to the shaft in such a way that the shaft is widened in the region of the handle, i.e. the outer side of the instrument, facing away from the handle, has a step in the region of the handle extension.

In addition, the eyepiece cup is arranged at the proximal end of the shaft in such a way that the longitudinal center axis of the eyepiece cup runs as a straight-line coaxial extension of the longitudinal center axis of the instrument shaft, so that the eyepiece cup extends circumferentially beyond the shaft on all sides.

This configuration of the known instrument is, however, disadvantageous in the context of a surgical procedure for removing the great saphenous vein.

This is because in the endoscopic procedure for removal of the great saphenous vein, the instrument is introduced through the incision in the knee region and is pushed upward along the vein to the groin, and downward into the ankle region.

In order to allow the entire vein to be removed through a single incision, the entire length of the medical instrument must be utilized, since the instrument must be advanced from the knee into the groin and down to the ankle along the vein. Since the vein runs just beneath the skin, the shaft of the instrument must be advanced almost parallel to the skin surface, so that the segment of the shaft located outside the incision as the shaft is advanced along the vein must be pushed forward while being held as closely as possible against the leg.

With the known instrument, the fact that the attachment segment of the handle and the eyepiece, as described above, project laterally in the proximal region of the shaft that remains outside the body means that the instrument is considerably widened in its proximal region above the shaft on the outer side of the instrument that rests against the leg. This widening, however, prevents the instrument from lying close to the patient's leg, with the consequence that the spatula tip cannot be slid forward along the vein just beneath the skin surface. Such is the case, at least, when the instrument has already been advanced a long way into the operative area. Because of the widening of the instrument in the proximal region on the outer side facing away from the handle, it is thus almost impossible to guide the spatula tip deep into the operative area along the saphenous vein while still parallel to the skin surface. Instead, the spatula tip penetrates into deeper tissue and can thereby result in undesirable damage to uninvolved tissue. To eliminate this risk, the known instrument can be used only up to a certain insertion depth of the shaft into the operative area. A further disadvantage of the known instrument furthermore consists in the fact that with increasing insertion depth of the shaft into the incision, the camera connected to the eyepiece for observation of the operation through the endoscopic optical system is, beyond a certain insertion depth, in such close contact against the patient's leg that the camera, whose housing dimension transverse to the shaft axis is wider than the shaft itself, prevents parallel subcutaneous advancement of the instrument. The camera furthermore prevents the introduction of further auxiliary instruments into the incision. Handling of the known instrument is thus also made more difficult.

U.S. Pat. No. 5,667,480 also discloses an instrument and method for endoscopic removal of the saphenous vein in which the aforesaid disadvantages also exist, namely that the shaft is widened in the region of the handle attachment, and that the eyepiece is axially aligned.

U.S. Pat. No. 5,373,840 discloses a comparable instrument, having a handle protruding laterally from the shaft and having an integrated endoscopic optical system that transfers the observed image directly to a monitor. An eyepiece can also be provided in conventional fashion instead of the monitor, but there is no indication as to how the eyepiece would then be arranged.

Against this background, it is the object of the present invention to make available a medical instrument of the aforesaid kind which makes it possible to remove the great saphenous vein through the smallest possible incision in the patient's body, the spatula tip of the instrument is to be insertable into the incision and along the vein just beneath the skin surface over as much as possible of the entire insertion depth of the shaft.

SUMMARY OF THE INVENTION

This object is achieved, in terms of the medical instrument cited initially, in that the handle is joined to the shaft in such a way that an outer side of the instrument facing away from the handle has a continuous straight surface that, from the distal to the proximal end, is substantially free of projections, and that the eyepiece cup is inclined with respect to a longitudinal center axis of the shaft and encloses with the handle an angle of less than 90° with respect to the longitudinal center axis.

As a result of the design according to the present invention, the medical instrument receives on its outer side facing away from the handle a uniform surface, running from the proximal end to the beginning of the distal spatula tip, that is free of projections and thereby allows the proximal region of the instrument to lie in close contact against the outer surface of the patient's leg, and thus readily permits the shaft of the spatula tip to be slid along the vein just beneath the skin surface. Because the eyepiece cup is arranged, according to the present invention, in laterally oblique fashion, it also no longer extends beyond the outer side of the instrument facing away from the handle.

The design according to the present invention, having an outer side that is free of projections, makes it possible to introduce the medical instrument into the patient's leg over the entire length of its shaft. Since there are no enlargements, ridges, or the like in the proximal region of the instrument, the instrument can be introduced in closely contacting fashion in the region of the incision and held in that fashion during the operation. The instrument according to the present invention thus makes it possible, even with a small incision, to utilize the entire length of the shaft.

This uniform surface also allows easy insertion of further auxiliary instruments, for example vein dissectors, dissecting or grasping forceps, scissors, ligature loops, or the like, without requiring a larger incision.

The aforesaid outer side of the medical instrument according to the present invention need not be continuously integral. It can be constituted from multiple surfaces, arranged one behind another, which belong to different constituents of the instrument (such as the endoscope, handle, and shaft) that optionally are detachable from one another. What is critical in this context is that the aforesaid outer side is free of projections that protrude distinctly beyond the outer periphery of the shaft. The medical instrument is thus of substantially flat configuration on the side resting against the patient's leg, and the instrument is slid into the incision along the patient's leg on that outer side.

A further advantage of the instrument according to the present invention is the fact that the physician can always bring his or her eye to the eyepiece cup in unimpeded fashion regardless of the insertion depth of the instrument, since the eyepiece cup stands out from the shaft and thus from the patient's leg. In the event a camera is used on the instrument eyepiece, introduction of the auxiliary instruments is advantageously no longer impeded by the attached camera. As an additional result, handling of the instrument according to the present invention is advantageously improved.

The method of the present invention includes the step of providing an instrument according to the present invention.

In a preferred embodiment, the handle has an attachment segment that is configured in the upper region in the form of a sleeve which fits over an axial portion of the shaft with the least possible material thickness on the outer side of the shaft facing away from the handle.

This feature has the advantage on the one hand of bringing about a stable join between the handle and the shaft, and on the other hand of keeping the outer side of the instrument, facing away from the handle, free of shoulders, steps, or protrusions.

In a further preferred embodiment, a longitudinal center axis of the eyepiece cup forms an angle in the range from 30° to 60°, preferably 45°, with the longitudinal center axis of the shaft.

If the eyepiece cup is arranged to protrude at an angle within this range, it is particularly convenient for the physician to look into the eyepiece cup from the side of the instrument facing away from the patient's body.

In a further preferred embodiment, the eyepiece cup is arranged on an eyepiece housing of the endoscopic optical system which has an outer side, facing away from the eyepiece cup, that approximately aligns with the outer side of the shaft facing away from the handle.

The advantage of this feature is that the aforesaid outer side of the eyepiece housing constitutes a shoulder-free prolongation of the outer side of the instrument facing away from the handle, thus improving guidance of the instrument along the leg by way of the extended contact surface constituted by the eyepiece housing.

In a further preferred embodiment, the shaft is configured as a circumferentially closed hollow shaft for reception of an optical shaft, extending to the spatula tip, of the endoscopic optical system.

The advantage of this feature is that the optical shaft of the endoscopic optical system received in the shaft experiences improved guidance upon insertion along the shaft and improved retention in the shaft, thus facilitating installation of the endoscopic optical system on the instrument shaft. A closed shaft having an internally located optical shaft moreover has the advantage that the outer surface of the shaft can be configured to be smooth and have no sharp edges all around, thus allowing the shaft to be more easily advanced in the operative area. The optical shaft is moreover protected from contamination. In addition, further auxiliary instruments can be introduced into the instrument shaft in order to remove connecting tissue and detach the vein. All these auxiliary instruments can then be enclosed by the shaft and thus also protected from contamination. Above all, the instruments experience "non-jerky" guidance along the shaft toward the distal end.

In a further preferred embodiment, the outer side of the shaft facing away from the handle is flat in cross section, viewed toward the longitudinal center axis of the shaft, with a slight concave curvature.

Since the outer side of the shaft facing away from the handle is guided along the outer surface of the leg upon insertion of the instrument, the advantage of this feature is that this outer side rests in planar contact against the leg and thus allows improved guidance of the shaft along the leg. The slightly concave configuration additionally has the advantage that the segment of the shaft already introduced into the incision experiences, with the curvature, a certain positive guidance along the vein.

In a further preferred embodiment, an outer side of the shaft facing toward the handle is convexly curved in cross section when viewed toward the longitudinal center axis of the shaft.

The advantage of this feature is that the optical shaft received in the shaft automatically assumes a centered position in the instrument shaft in the curvature upon insertion into the shaft, thus further facilitating installation of the endoscopic optical system on the shaft.

In a further preferred embodiment, the spatula tip has a spoon-shaped curvature that opens toward the side of the instrument facing away from the handle.

The advantage here is that as the instrument is slid forward, an operative cavity, which can be easily illuminated and observed through the endoscopic optical system, is formed in the region of the distal spatula tip. The spoon-shaped curvature of the spatula tip also protects the region in which the distal elements of the auxiliary instruments, for example mouth parts of forceps of the like, are actuated.

In a further preferred embodiment, the spatula tip has a lateral widening so that it extends beyond the shaft, at least on one side, transversely to its longitudinal center axis.

The advantage of this feature is that the operative cavity created by the spatula tip as the shaft is advanced is enlarged as compared to the operative cavity created by the spatula tip of the known instrument. An enlarged operative cavity has the advantage that more space is created for the mouth parts of the auxiliary instruments.

In a further preferred embodiment, the spatula tip tapers toward the distal end.

The advantage of this tapering is that it facilitates advancement of the instrument according to the present invention through the bodily tissue.

In a further preferred embodiment, the handle projects from the shaft obliquely toward the distal end of the shaft.

The advantage of this feature is that the instrument can be introduced into the incision, at the handle which is thus inclined in the insertion direction, with a straight hand position and thus forcefully, thus further improving handling of the instrument according to the present invention.

In a further preferred embodiment, the handle encloses with the eyepiece cup an angle of less than 10°, preferably approximately 0°, in terms of the longitudinal center axis.

With this embodiment, the handle and the eyepiece cup thus protrude from the shaft in a single plane, thus achieving the advantage that after introduction of the instrument, it can also be rotated about its longitudinal axis without thereby encountering the eyepiece cup as an obstacle. Rotation of the instrument as it is advanced may be used, for example to deflect side branches of the saphenous vein as the instrument is advanced.

Further advantages are evident from the description below and from the appended drawings.

It is understood that the features mentioned above and those yet to be explained below can be used not only in the respective combinations indicated, but also in other combinations or in isolation, without leaving the context of the present invention.

BRIEF DESCRIPTION OF THE DRAWINGS

An exemplary embodiment of the invention will be explained in more detail below with reference to the drawings, in which:

FIG. 4 shows a schematic presentation to explain the method for removing the saphenous vein from a leg; and FIGS. 5 and 6 show the distal end of a vein dissector that is used to remove the great saphenous vein, FIG. 5 being a plan view and FIG. 6 a front view.

DETAILED DESCRIPTION OF A PREFERRED EMBODIMENT

Figure 1:
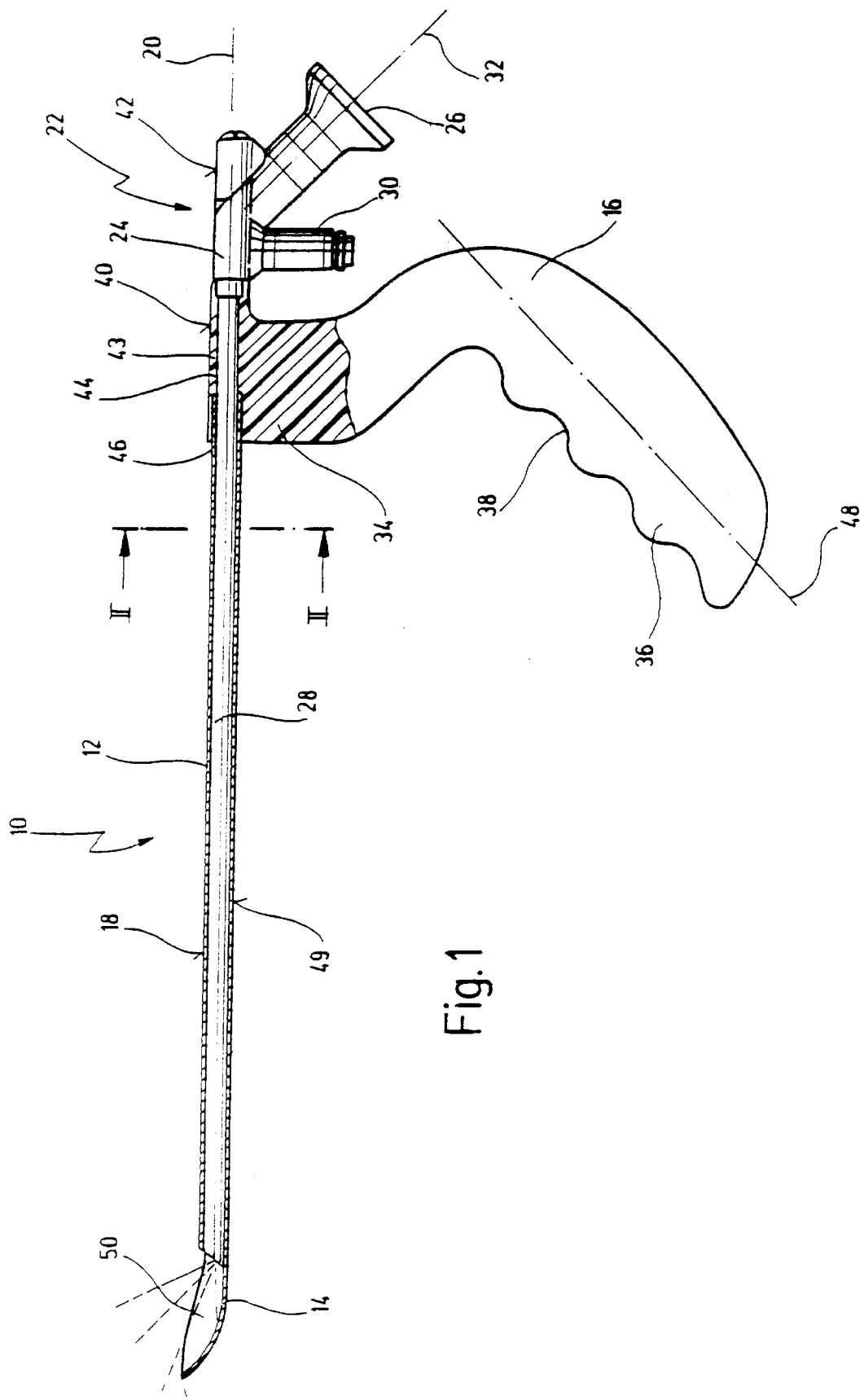
FIG. 1 shows a side view of a medical instrument according to the present invention, partially in a longitudinal section.
Figure 2:
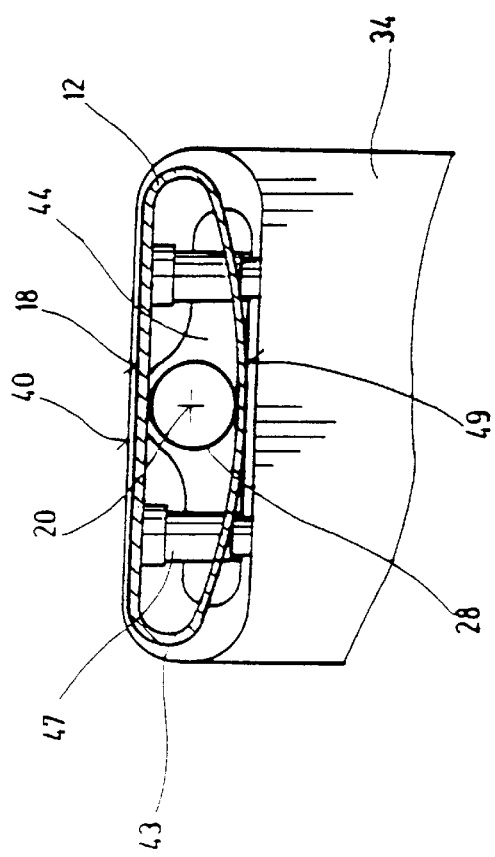
FIG. 2 shows a section through the instrument along line II—II in FIG. 1, at enlarged scale.

FIGS. 1 and 2 depict a medical instrument, labeled with the general reference character 10, for removing the saphenous vein (vena saphena magna).

Medical instrument 10 has an elongated shaft 12 which carries at its distal end a spatula tip 14 and in whose proximal region is arranged a handle 16 that protrudes laterally from shaft 12.

Shaft 12 has an outer side 18 facing away from handle 16. Outer side 18 is that side which, upon introduction of shaft 12 into the leg of a patient, rests against the outside of the leg with its region located outside the incision, and whose already-inserted region is guided along the vein.

As is evident from FIG. 2, outer side 18 is of substantially flat configuration in cross section, viewed toward a longitudinal center axis 20 of shaft 10, with a slight concave curvature.

Figure 3:
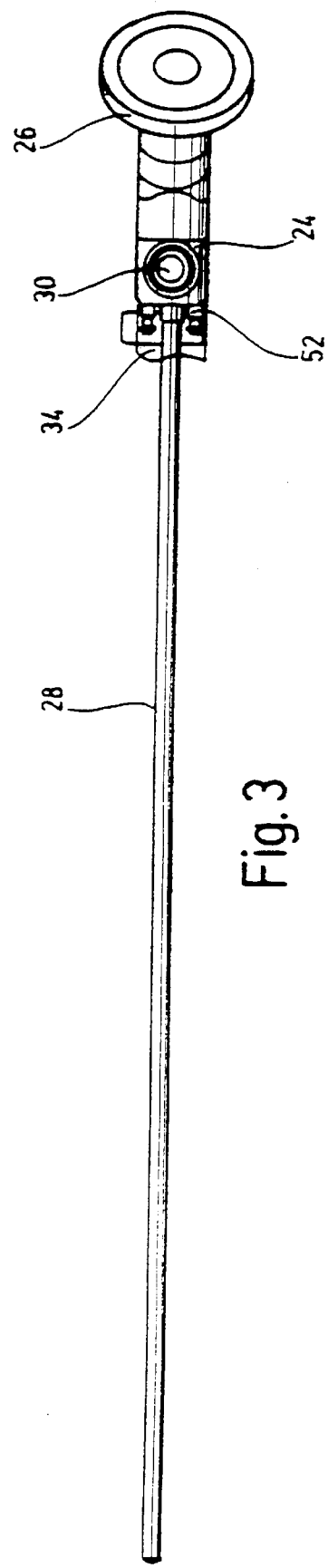
FIG. 3 shows a plan view of the endoscopic optical system received by the instrument in FIG. 1.

Instrument 10 furthermore has an endoscopic optical system 22, removable from shaft 12 and from handle 16, that is shown in FIG. 3 in isolation, removed from shaft 12.

Endoscopic optical system 22 has at the proximal end an eyepiece housing 24 having an eyepiece cup 26. Adjoining eyepiece housing 24 distally is an optical shaft 28. Optical shaft 28 is configured as a cylindrical tube in which an optically imaging system, comprising a lens system, aperture stops, filters, etc. or a coherent optical fiber bundle, is arranged. Also arranged in optical shaft 28 is a lightdelivering fiber bundle with which light is delivered into the operative area. Provided for that purpose on eyepiece housing 24 is a connector 30 for attaching a fiber optic cable (not shown) that can be connected to a light source (not shown).

When endoscopic optical system 22 is mounted on shaft 12, eyepiece cup 26 is arranged on the same side as handle 16, directed obliquely, with respect to longitudinal center axis 20 of shaft 12, toward the proximal end. Handle 16 encloses with eyepiece cup 26, in terms of longitudinal center axis 20, an angle of less than 90° (0° in the exemplary embodiment shown).

In this context, a longitudinal center axis 32 of eyepiece cup 26 forms an angle in the range from 30° to 60°—in FIG. 1 an angle of approximately 45°—with longitudinal center axis 20 of shaft 12.

Connector 30 for attaching the fiber optic cable protrudes approximately at right angles from instrument 10 on the same side as handle 16 and eyepiece cup 26.

Handle 16 comprises an attachment segment 34 that runs approximately at right angles to shaft 12, and an actual handle segment 36 that has finger recesses 38.

Handle 16 is joined to shaft 12 in such a way that outer side 18 of shaft 12 facing away from handle 16 forms, in the region of attachment segment 34 of handle 16 and with an outer side 40 of attachment segment 34, a substantially uniform surface that is substantially free of projections or shoulders.

Eyepiece housing 24 similarly has a corresponding outer side 42 that proximally adjoins outer side 40 of attachment segment 34 of handle 16 and thus approximately aligns with outer side 18 of the shaft.

The entire outer side of instrument 10, composed of outer sides 18, 40, 42, thus has a uniform surface from the distal to the proximal end, i.e. a surface that exhibits no irregularities in the form of shoulders or projections.

Attachment segment 34 has in the upper region a configuration in the form of a sleeve 43 having an axially continuous opening 44 through which optical shaft 28 is passed. In the distal region of attachment segment 34, a segment 46 of opening 44 is configured in accordance with the outer contour of shaft 12, so that shaft 12 can be inserted into the distal end of attachment segment 34 of handle 16.

Shaft 12 and handle 16 are joined to one another in lossproof fashion by way of screws 47 that pass through attachment segment 34 and shaft 12 and do not project toward outer side 40. Sleeve 43 of attachment segment 34 fits around shaft 12 with a thin material thickness on outer side 18 facing away from handle 16, so that attachment segment 34 substantially does not project beyond shaft 12 on outer side 18. The aforesaid material thickness has precisely the dimension necessary for secure attachment of handle 16 to shaft 12.

Handle 16, or more precisely handle segment 36 of handle 16, protrudes obliquely toward the distal end from shaft 12, so that a longitudinal center axis 48 of handle 16 forms an angle of approximately 45° with longitudinal center axis 20 of instrument 10 when viewed toward the distal end.

As is further evident from FIG. 2, shaft 12 is configured as a circumferentially closed hollow shaft having optical shaft 28 of endoscopic optical system 22 received in its interior.

An outer side 49 of shaft 12 facing toward handle 16, which lies opposite outer side 18, is convexly curved in cross section when viewed toward longitudinal center axis 20.

Because of this convex curvature of outer side 49, and also because of the slight concave curvature of outer side 18, optical shaft 28 is received in shaft 12 centeredly with respect to longitudinal center axis 20.

Overall, shaft 12 is configured in cross section as a flat oval or a very slight kidney shape.

Also present in shaft 12, on both sides of optical shaft 28, is an axially continuous open space for the introduction of auxiliary instruments that are used to remove the great saphenous vein, for example vein dissectors, grasping forceps, or the like.

Endoscope shaft 28 extends distally as far as spatula tip 14. Spatula tip 14 has a spoon-shaped curvature that opens toward outer side 18 of shaft 12. Spatula tip 14 also tapers toward the distal end. A lateral widening 50 is configured such that spatula tip 14 extends slightly beyond shaft 12 toward outer side 18.

For quick-release attachment and locking of endoscopic optical system 22 to attachment segment 34 of handle 16, two axially projecting pins 52, which can be brought into engagement with corresponding cutouts in attachment segment 34 of handle 16 and locked, are provided on eyepiece housing 24.

A method for removing the saphenous vein in which instrument 10 is used will now be described with reference to FIG. 4.

FIG. 4 schematically shows the left leg 60 of a patient. Great saphenous vein 62, which is indicated in FIG. 4 with dashed lines, extends subcutaneously from ankle region 64 through lower leg 66, past knee 68, and through thigh 70 into groin 72. Saphenous vein 62 runs along the inner side of leg 60.

The removal method described hereinafter makes it possible to remove saphenous vein 62 through two incisions 74 and 76, and in fact in principle through only one of incisions 74 or 76.

After anesthetization, the patient is positioned supine on the operating table, leg 70 being rotated slightly outward.

If great saphenous vein 62 is to be removed principally from thigh 70 and only partially from lower leg 66, only incision 74 is necessary; this is made with a scalpel, as a transverse incision, slightly above knee 68. If great saphenous vein 62 is to be removed principally from lower leg 66 and only partially from thigh 70, only incision 76 is necessary; this is made as a transverse incision slightly below knee 68.

If the entire saphenous vein 62, from ankle region 64 to groin 72, is to be removed, it is more favorable if both incisions 74 and 76 are made.

"Transverse incision" is understood to mean that the cuts are made transverse to the longitudinal direction of thigh 70 or the longitudinal direction of lower leg 66. The length of the incisions is approximately 2 to 3 cm.

As is evident from FIG. 4, incisions 74 and 76 are located in the immediate vicinity of saphenous vein 62.

Incision 74 and/or 76 is first opened up down to saphenous vein 62.

Instrument 10 in FIGS. 1 through 3 is then fitted with endoscopic optical system 22. A video camera, connected to a monitor on which the endoscopic image is observed, is connected via an adapter to eyepiece cup 26.

Mobilization of saphenous vein 62 in the thigh then begins, the first step being to create, using instrument 10 in FIGS. 1 through 3, a subcutaneous channel or cavity along the great saphenous vein.

This is done by inserting instrument 10, with spatula tip 14, into incision 74. Outer side 18 of shaft 12 facing away from handle 16 thereby rests against knee 68, and spatula tip 14 points toward groin 72.

Instrument 10 is then slowly and carefully advanced, under endoscopic visual supervision on the monitor, along saphenous vein 62 toward groin 72.

Spatula tip 14 thereby creates a subcutaneous channel or cavity along saphenous vein 62. As spatula tip 14 is advanced, endoscopic visual supervision is used to ensure that no undesired additional subcutaneous channels are created.

In order to make way for side branches of saphenous vein 62 as instrument 10 is advanced, instrument 10 is correspondingly rotated slightly as it is advanced along saphenous vein 62.

If saphenous vein 62 is to be removed all the way to groin 72, instrument 10 is advanced along vein 62 until spatula tip 14 has reached groin 72; otherwise it is kept at the intended removal endpoint.

A subcutaneous channel has now been created along saphenous vein 62, and saphenous vein 62 will subsequently be detached from its side branches.

For this purpose, while instrument 10 remains inserted, additional instruments such as scissors are introduced into incision 74 in order to cut saphenous vein 62 off from its side branches.

Before the side branches are cut through, they are clamped in situ with a clamp applicator (not shown) in order to interrupt the blood flow.

High-frequency current-assisted instruments, such as bipolar or monopolar scissors, are particularly suitable for cutting, since bleeding can be avoided to the greatest possible extent when such instruments are used. This is because the stubs of the side branches can be simultaneously coagulated by the action of the high-frequency current.

Once saphenous vein 62 in thigh 70 has been detached from its side branches, instrument 10 is kept inserted and a vein dissector 78, shown in FIG. 5 and 6, is introduced; its distal end has an eye 80 curved transversely to the longitudinal direction of the instrument in approximately the shape of a semicircle or three-quarter circle.

After insertion through incision 74, eye 80 is placed around saphenous vein 62 and instrument 78 is then advanced along saphenous vein 62 to groin 72, thereby scraping away from great saphenous vein 62 any subcutaneous tissue that is still adhering.

Saphenous vein 62 is now completely mobilized, but has not yet been cut through at its end in groin 72.

All the aforesaid actions, i.e. detaching great saphenous vein 62 from its side branches and detaching great saphenous vein 62 from the attached subcutaneous tissue, take place with continuous visual supervision on the monitor via endoscopic optical system 22 of instrument 10, which remains in place in the operative area during these actions. In this context, instrument 10 is in each case positioned, by being advanced or pulled back, so that spatula tip 14 is located at those particular points at which dissection is currently being performed.

The spoon-like widened configuration of spatula tip 14, in particular widening 50, forms in each case a cavity in which it is then possible to work in a correspondingly safe manner, as described above, with the applicator, the respective cutting instrument, or the dissector.

Following complete mobilization of great saphenous vein 62 in the thigh, instrument 10 is taken out of incision 74 and introduced once again into incision 74 but with spatula tip 14 pointing toward ankle region 64, after which the same actions described above are performed to mobilize saphenous vein 62 in the lower leg.

If removal is to occur all the way to ankle region 64, incision 76 is better suited for this purpose.

Following complete mobilization of saphenous vein 62 in lower leg 66, saphenous vein 62 is temporarily pulled slightly out of incision 76 or 74. A suture is placed around the pulled-out portion and tied into a loop that can be tightened.

The loop, not yet tightened, is then slid along great saphenous vein 64 to ankle region 64 using vein dissector 78, under endoscopic supervision via instrument 10.

At ankle 64, the loop is then tightened in order to tie off great saphenous vein 62 at ankle region 64.

Saphenous vein 62 is then cut through with a scissors in front of the loop (as viewed from knee 68). The detached lower-leg segment of saphenous vein 62 can then be pulled out through incision 74 or 76.

The same procedure described above is then performed in thigh 70 in order to tie off saphenous vein 62 in the region of groin 72 and detach it at a point in front. Saphenous vein 62 is now completely detached and is pulled completely out of leg 60 through incision 76 or 74.

Saphenous vein 62 removed in this fashion is then available for a bypass operation.

Saphenous vein 62 can be appropriately stored in a solution until it is used in the bypass operation.

Incision 74 and/or incision 76 are then appropriately sutured, and leg 60 is wrapped in an elastic bandage for twenty-four hours.

What is claimed, is:

1. A medical instrument for endoscopic removal of the saphenous vein, comprising
   an elongated shaft;
   a spatula tip at a distal end of said shaft;
   a handle disposed in a proximal region of said shaft and affixed thereto, said handle projecting laterally from said shaft;
   an endoscopic optical system comprising an eyepiece cup arranged at a proximal end of said instrument;
      wherein said handle is joined to said shaft in such a way that an outer side of said instrument facing away from said handle has a continuous straight surface that, from the distal to the proximal end, is free of projections,
      said eyepiece cup is arranged on an eyepiece housing of said endoscopic optical system which has an outer side, facing away from said eyepiece cup, that approximately aligns with said outer side of said shaft facing away from said handle, and
      a longitudinal center axis of said eyepiece cup is inclined with respect to a longitudinal center axis of said shaft at an angle of less than 90°.

2. The instrument of claim 1, wherein said handle has an attachment segment that is configured in its upper region in the form of a sleeve which fits over an axial portion of said shaft with the least possible material thickness on said outer side of said shaft facing away from said handle.

3. The instrument of claim 1, wherein a longitudinal center axis of said eyepiece cup forms an angle in the range from 30° to 60°, preferably 45°, with said longitudinal center axis of said shaft.

4. The instrument of claim 1, wherein said shaft is configured as a circumferentially closed hollow shaft for reception of an optical shaft, extending to said spatula tip, of said endoscopic optical system.

5. The instrument of claim 1, wherein said outer side of said shaft facing away from said handle is configured with a slight concave curvature in cross section when viewed toward said longitudinal center axis of said shaft.

6. The instrument of claim 1, wherein an outer side of said shaft facing toward said handle is convexly curved in cross section when viewed toward said longitudinal center axis of said shaft.

7. The instrument of claim 1, wherein said spatula tip has a spoon-shaped curvature that opens toward said outer side of said instrument facing away from said handle.

8. The instrument of claim 1, wherein said spatula tip has a lateral widening so that it extends beyond said shaft, at least on one side, transversely to its longitudinal center axis.

9. The instrument of claim 1, wherein said spatula tip tapers toward its distal end.

10. The instrument of claim 1, wherein said handle projects from said shaft obliquely toward said distal end of said shaft.

11. A method for endoscopic removal of the saphenous vein from a patient's leg, including the steps:

providing an instrument, comprising
an elongated shaft;
a spatula tip at a distal end of said shaft;
a handle disposed in a proximal region of said shaft and affixed thereto, said handle projecting laterally from said shaft;
an endoscopic optical system comprising an eyepiece cup arranged at a proximal end of said instrument;
wherein said handle is joined to said shaft in such a way that an outer side of said instrument facing away from said handle has a continuous straight surface that, from the distal to the proximal end, is free of projections,
said eyepiece cup is arranged on an eyepiece housing of said endoscopic optical system which has an outer side, facing away from said eyepiece cup, that approximately aligns with said outer side of said shaft facing away from said handle, and
a longitudinal center axis of said eyepiece cup is inclined with respect to a longitudinal center axis of said shaft at an angle of less than 90°;

making an incision near the saphenous vein in the patient's leg;

introducing said instrument into said incision and advancing said instrument under visual supervision though said endscopic optical system along said vein thereby creating a subcutaneous channel along said saphenous vein.

12. The method of claim 11, wherein after creating said subcutaneous channel side branches of said vein are detached by means of at least one cutting instrument, which is introduced into said shaft of said instrument while kept inserted in the patient's leg.

13. The method of claim 12, wherein after detaching said side branches a vein dissector having an eye curved transversely to a longitudinal direction of said vein dissector is introduced into said insection, said eye is placed around said saphenous vein and advanced along said vein thereby scraping away subcutaneous tissue adhering at the saphenous vein, said advancing of said vein dissector taking place under visual supervision through said endoscopic optical system of said instrument while kept inserted in the patient's leg.

* * * * *